United States Patent [19]

Stevens David R. et al.

[11] Patent Number: 4,983,786
[45] Date of Patent: Jan. 8, 1991

[54] XY VELOCITY CONTROLLER

[75] Inventors: Stevens David R., Vancouver; Andrea Marziali, North Vancouver, both of Canada

[73] Assignee: The University of British Columbia, Vancouver, Canada

[21] Appl. No.: 466,488

[22] Filed: Jan. 17, 1990

[51] Int. Cl.$^5$ .............................................. G08C 21/00
[52] U.S. Cl. ....................................... 178/18; 340/709
[58] Field of Search ..................... 178/18, 19; 340/709

[56] References Cited

U.S. PATENT DOCUMENTS

| | | | |
|---|---|---|---|
| 4,484,026 | 11/1984 | Thornburg | 178/18 |
| 4,529,959 | 7/1987 | Kazuhiko et al. | 178/18 X |
| 4,687,885 | 8/1987 | Talmage et al. | 178/18 |
| 4,728,812 | 3/1988 | Sheriff | 307/134 |

OTHER PUBLICATIONS

Force Sensing Resistors–Interlink Electronics, Santa Barbara, CA.

Primary Examiner—Stafford D. Schreyer
Attorney, Agent, or Firm—C. A. Rowley

[57] ABSTRACT

A XY control system for controlling vector movement in two mutually perpendicular directions (for example for computer cursor control, i.e. emulating a conventional computer mouse) uses a XY pressure sensitive digital pad or more preferably a XYZ pressure sensitive digital pad generating different signals based on the selected location at which pressure is applied to the pad. These signals are divided into X or Y and a directional signal and then converted into a velocity signal for controlling the vector motion in the required direction dependent on the selected location for application of pressure to the pad and at a velocity the magnitude of which is proportional to the displacement of the selected location from a datum area on the pad, or in the case of a XYZ pad dependent on both displacement and the amount of pressure applied at the selected location.

10 Claims, 3 Drawing Sheets

XY VELOCITY CONTROLLER

FIELD OF THE INVENTION

The present invention relates to a XY controller. More particularly the present invention relates to a control for vector movement in two mutually perpendicular directions, wherein X or Y directional signals, as well as signals governing the magnitude of the velocity are generated that are proportional to the selected location of a point of application of pressure to a xy pressure sensitive digital pad relative to a datum on the pad and/or the amount of pressure applied at the point to a XYZ pressure sensitive pad.

BACKGROUND OF THE PRESENT INVENTION

Many handicapped persons are extremely limited in their ability to communicate due their inability to control limb movement. Attempts (some successful) have been made to provide ways requiring minimal muscular input from the operator to control the performance of simple routine tasks and thereby better enabling disabled persons to have a further degree of independence. Generally existing systems are relatively slow and difficult or tedious to operate, particular over sustained periods.

In a limited number of cases a computer has been successfully used by handicapped people, however such use is limited by the lack of an appropriate interface between the computer and the handicapped person. Normally in-putting the computer requires some degree of manual dexterity and involves for example keyboard or computer mouse input. When the hands are restricted or not available these input devices are not satisfactory.

Some solutions assume the that user has normal function of the neck and head, but there are many disabled persons that can not control those muscles. Some are able only to control their mouth and tongue and some also are inflicted with spastic motion, making the interface between such persons with a computer even more difficult.

The most common solution to the interfacing problem for persons having control of head and neck is the tapping stick. The user simply grips one end of the stick in his mouth and taps the opposite end on the keyboard. Users can become quite proficient and the cost of this solution is relatively low since no modifications to the computer are required. However, the system is limited as such a user faces great if not insurmountable difficulty in operating the control functions that require the manipulation of more than one key simultaneously.

Those individuals who do not have these faculties and can only control their mouth have few avenues available. Speech recognizing systems have been used, but are extremely expensive and very limited in effectiveness. The most popular interface uses a puff-suck tube which is held in the mouth like a straw and a sequence of pressure fluctuations caused by blowing and sucking are detected and used, for example, as a switch (binary system) or to generate a sequence representing some form of code such as Morse code. These code signals are then translated into computer inputs.

None of these systems are suitable for cursor control in the way a computer mouse for example can be used to interface with a computer. If the handicapped person has the ability to move the cursor over the screen of the monitor and then at the appropriate location to make a selection by activating for example an on-off switch as with the computer mouse a whole new realm of communication would be possible. This would enable a severely handicapped person to operate much more complicated software programs such as graphics or drawing packages or the like and could also be used to control various appliances throughout the house such as the telephone, lights, stereo, television, etc. by activating same through window displays on the computer.

It has been suggested to use the tongue as the operating element for controlling a potentiometer as described in U.S. Pat. No. 4,728,812 issued to Sheriff et al Mar. 1, 1988. This device controls the operation of a machine by jaw and tongue movement of the operator. The control is effected by movement of the jaws which moves a pair of levers to adjust the contacts of a potentiometer. A tongue actuated micro switch is provided for added control. Such a device is useful for some purposes.

U.S. Pat. Nos. 4,484,026 to Thornburg issued Nov. 20, 1984 and 4,529,959 issued to July 16, 1987 to Kazuhiko et al disclose various digitizer control pads. Interlink Electronics 1110 Monk Avenue, Carpinteria Calif. 93105 offer a line of force sensing resistors and XY and XYZ digitizer pads that may be applied to various applications.

BRIEF DESCRIPTION OF THE PREFERRED INVENTION

It is an object of the present invention to provide an XY velocity control system requiring limited muscular movement.

It is a preferred object of the present invention to provide a mouth controlled XY directional velocity control for control of vector movement in two mutually perpendicular directions wherein the velocity and direction of movement are dependent on the location of a point of pressure application (and amount of pressure applied) to a control surface.

Broadly the present invention relates to a XY control system for selecting direction and magnitude of velocity in said selected direction of a controlled means comprising a XY digital pad generating different signals depending on a selected activated location on said pad, electrical circuit means dividing said signals into a datum signal when said activated location on said pad is in a datum zone on said pad, a X signal when said activated location is displaced in a first direction from said datum zone, a Y signal when said activated location is displaced in a second direction perpendicular to said first direction from said datum zone and directional signals for said X and Y signals based on the side of said datum zone in said first and second directions respectively that said activated location is positioned on said pad, said electrical circuit means converting said X and Y signals into velocity signals proportional to the displacement of said activated location relative to said datum zone, and further electrical circuit means controlling said direction and magnitude of said velocity of said controlled means in accordance with said directional and said velocity signals.

Preferably said controlled means will be a computer cursor and said further circuit means will convert said directional and velocity signals to into said mutually perpendicular movements of the cursor on a computer monitor.

Preferably said digitizer pad will be pressure sensitive and said activated location will be activated by pressure applied to said pad at said activated location.

Preferably said digitizer pad will be an XYZ digitizer pad and said velocity signals will include a supplementary signal the magnitude of which is dependent on the amount of pressure applied to said pressure point.

Preferably said XYZ digital pad will be mounted on a support plate sized to be received in the mouth of a user with said pad in facing relationship to the user's tongue, said pad having a moisture resistant casing through which tongue pressure may be applied to generate said signals.

Preferably at least one pressure sensitive switch will be mounted on said support plate adjacent to said pad in a position to be activate by said tongue.

BRIEF DESCRIPTION OF THE DRAWINGS

Further features, objects and advantages will be evident from the following detailed description of the preferred embodiments of the present invention taken in conjunction with the accompanying drawings, in which.

DESCRIPTION OF THE PREFERRED EMBODIMENTS

The present invention is particularly adapted to provide a mouth (tongue) activated control system that is particularly suited to emulating a mouse type computer control and will be described as such hereinbelow, however, it will be evident that the directional and velocity signals generated by the control system could be used for other purposes.

Figure 1:
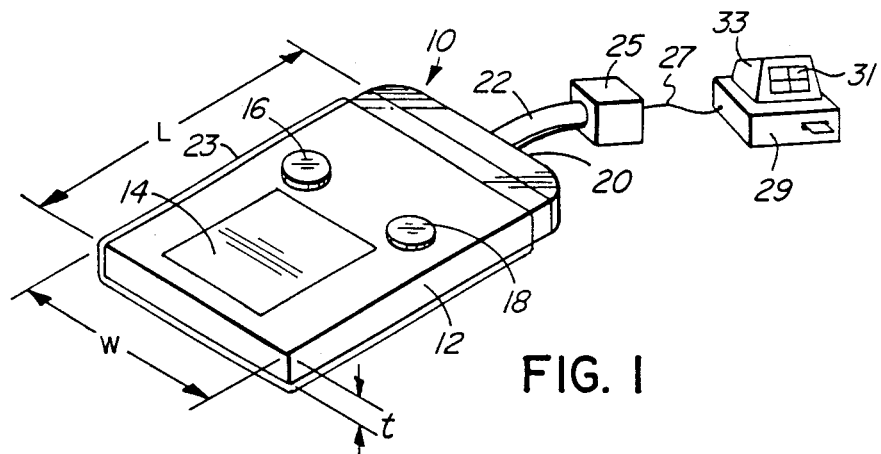
FIG. 1 is an isometric schematic illustration of controller constructed in accordance with the present invention.

As shown in FIG. 1 a preferred form of mouth controller element 10 comprises a support plate such as a rigid backing plate 12 having a XY digitizer pad or preferably a XYZ digitizer pad 14 mounted thereon. It is preferred that the digitizer pad be a pressure sensitive digitizer pad. A pair of pressure sensitive switches 16 and 18 are also mounted on the plate 12 adjacent the pad 14 in a position that either may selectively be activated with little muscular movement i.e. simple and short extension of the manipulating limb or part of the operator from the pad 14, for example by tongue pressure applied by slight extension of the tongue when the controller is in position in the mouth of a user. The pad 14 and switches 16 and 18 are electrically connected via the connector 20 and cable 22 to the computer interface circuitry contained in the unit 25 and then in the illustrated arrangement via line 27 to input the mouse card (not shown) contained in the computer 29. Input to the pad 14 and switches 16 and 18 by application of pressure at selected locations (activated locations) controls the movement of the cursor (in the illustration cross hair) 31 on the monitor 33.

The pad 14 and switches 16 and 18 may be constructed to be water proof and still be pressure sensitive, but it is preferred to also provide a throw away cover 23 in the form of a water proof bag (plastic) that surrounds the controller and is inexpensive so that it may be discarded after use. The bag also protects the pad 14 and switches 16 and 18 from moisture yet permits easy application of pressure therethrough.

The support plate 12 when the unit is used as a mouth controller is sized to fit easily within the mouth of a user, be comfortable therein and permit the tongue easily to reach the overall area of the digitizer pad 14 and the two pressure switches 16 and 18. It has been found that if the controller is to be gripped between the teeth the width W of the plate 12 should be sufficiently wide that the plate 12 on opposite sides of the pad 14 may be clamped between the teeth on each side of the mouth rather than be received between them so that the reaction force of the tongue operating the controller is resisted by the teeth rather than the roof of the mouth. A narrow plate 12 that fits between the teeth and bears against the roof of the mouth generates significant discomfort to the user. A width W of about 4 centimeters has been found satisfactory for most people. In a specific application of the invention to a person a denture type appliance may be provided for mounting the pad 14 in the mouth and the size of the support may be adjusted as desired.

The thickness t should be such that the plate can easily and comfortably be received in the mouth of the user and the length L of the plate 12 should be such that when the controller is in position in the mouth the connector 20 should be well outside of the mouth.

The pad 14 should have a minimum dimension of at least about 2 centimeters. The size of the area of the pad 14 has a bearing on the effective spatial resolution that can be obtained, generally within reasonable limits the larger the minimum dimension of the area of the pad 14 the better spatial resolution attainable.

The particular pad or sensor 14 selected by applicant is a XYZ force sensing resistor made by Interlink Electronics of Carpinteria CA. Such a device includes a pair of interdigitized conductor layers 24 and 26 separated by layer 28 which preferable is a force sensing layer the electrical resistance of which reduces as the pressure applied is increased (see FIG. 2.)

While it is preferred that the layer 28 be a force sensing layer a similar control may be obtained when the layer 28 is not a force sensitive layer but has a substantially constant electrical resistance regardless of the forces applied. The use of a mono-resistance layer eliminates one element of control thus a force sensitive layer is preferred so that the signal is varied both by position and degree of force (pressure) as will be described below rather than by position alone.

Figure 3:
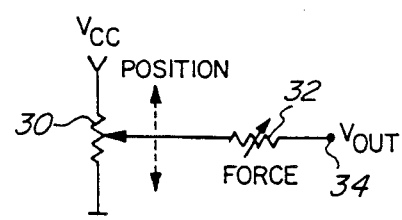
FIG. 3 is a typical circuit diagram for the digitizer pad of FIG. 2.
Figure 2:
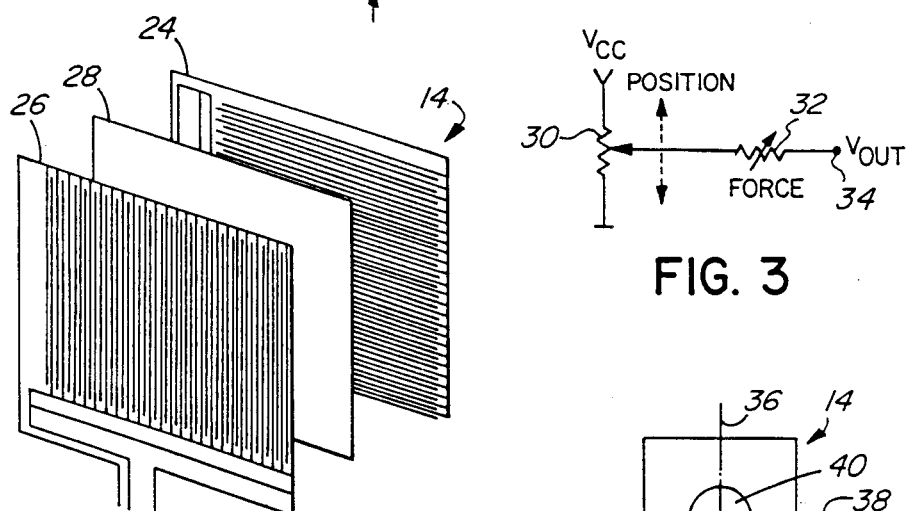
FIG. 2 is a schematic illustration of the construction of essential elements of an XYZ digitizer pad.

The digitizer pad 14 as illustrated in FIG. 2 incorporating a force sensing layer 28 acts as two perpendicular independent linear potentiometers, one operating in the X direction and one in the Y direction. The potentiometers are connected in a voltage divider configuration a shown in FIG. 3 wherein the resistance 30 represent one of the potentiometers 24 or 26 and the variable resistance 32 represents the force sensing layer 28.

With no current drawn at the output 34 the voltage out $V_{out}$ varies linearly from 0 to control voltage $V_{cc}$ depending on tongue position (activated location or pressure point on the pad) when an XY pressure sensitive digitizer pad is used and there is no influence due to tongue pressure (degree of pressure at the pressure point.) However, when current is allowed to flow with a digitizer pad 14 incorporating the variable resistance 32 which represents the force or pressure sensing membrane or layer 28, the tongue pressure applied to the sensor modulates the current flow at output 34.

Since the XYZ pad 14 acts as two perpendicular independent linear potentiometers one generating an X signal and the other a Y signal there are in effect two substantially identical and independent interface electrical circuits one for each direction, thus only one circuit will be described in detail.

Figure 4:
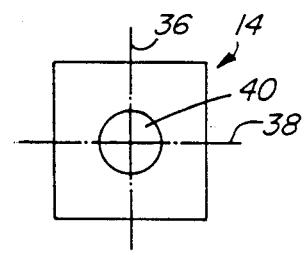
FIG. 4 is a plan view of a preferred mapping for digitizer pad used in the present invention illustrating the surface of the pad divided into quadrants and a central datum zone.
Figure 5:
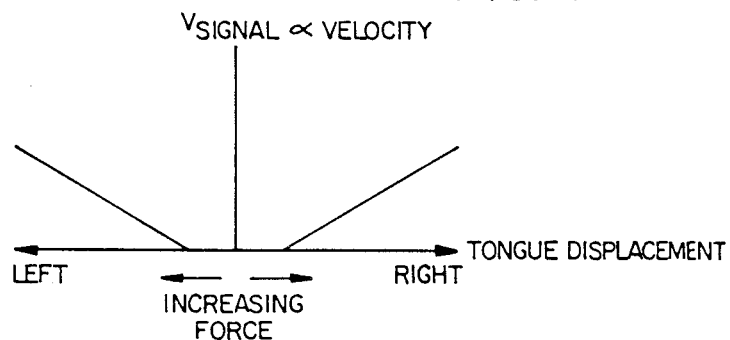
FIG. 5 is a graphic representation of the velocity signal changes with changes in position or degree of pressure application at the selected pressure point.

The digitizer pad 14 outputs a different signal depending on the activated location on the pad 14 and the electrical circuit (see FIG. 6) segregates these signals to in effect divide the surface of the pad into mapped areas as shown in FIG. 4 to permit the control pad 14 to function as an XY controller. In the illustrated system the area of the pad 14 is in effect divided into segments defined by a pair of mutually perpendicular axes 36 and 38 that function as datum zones for their respective X or Y signals and the intersection of which is surrounded by a datum area or zone 40. As will be described in more detail hereinbelow if pressure is applied within the datum zone or area 40 there is no effective signal generated. When pressure point (activated location) is applied to the pad 14 outside of the area 40 depending on the quadrant in which the pressure is applied a signal for movement up in the Y direction is generated when the pressure point location is above the line 38 or down in the Y direction when the location is below the line 38. Similarly when pressure is applied to the left of line 36 the potentiometer for the X direction will generate a signal for X direction movement to the left or if to the right of line 36 the signal is for movement to the right in the X direction.

In the particular arrangement described hereinbelow the distance between the location of the pressure point (activated location) and the datum zone or area 40 influences the signal output directly according to the distance. Similarly when a pressure sensing membrane 28 is used the amount of pressure also regulates the signal being generated directly with the amount of pressure applied. In all cases resolution of the activated location i.e. location of the pressure point (and magnitude of the pressure applied) dictates the strength of the X Y signals which determine the velocity of movement of the controlled element and not its position i.e. in the specific example the velocity of the cursor and not cursor position.

Figure 6:
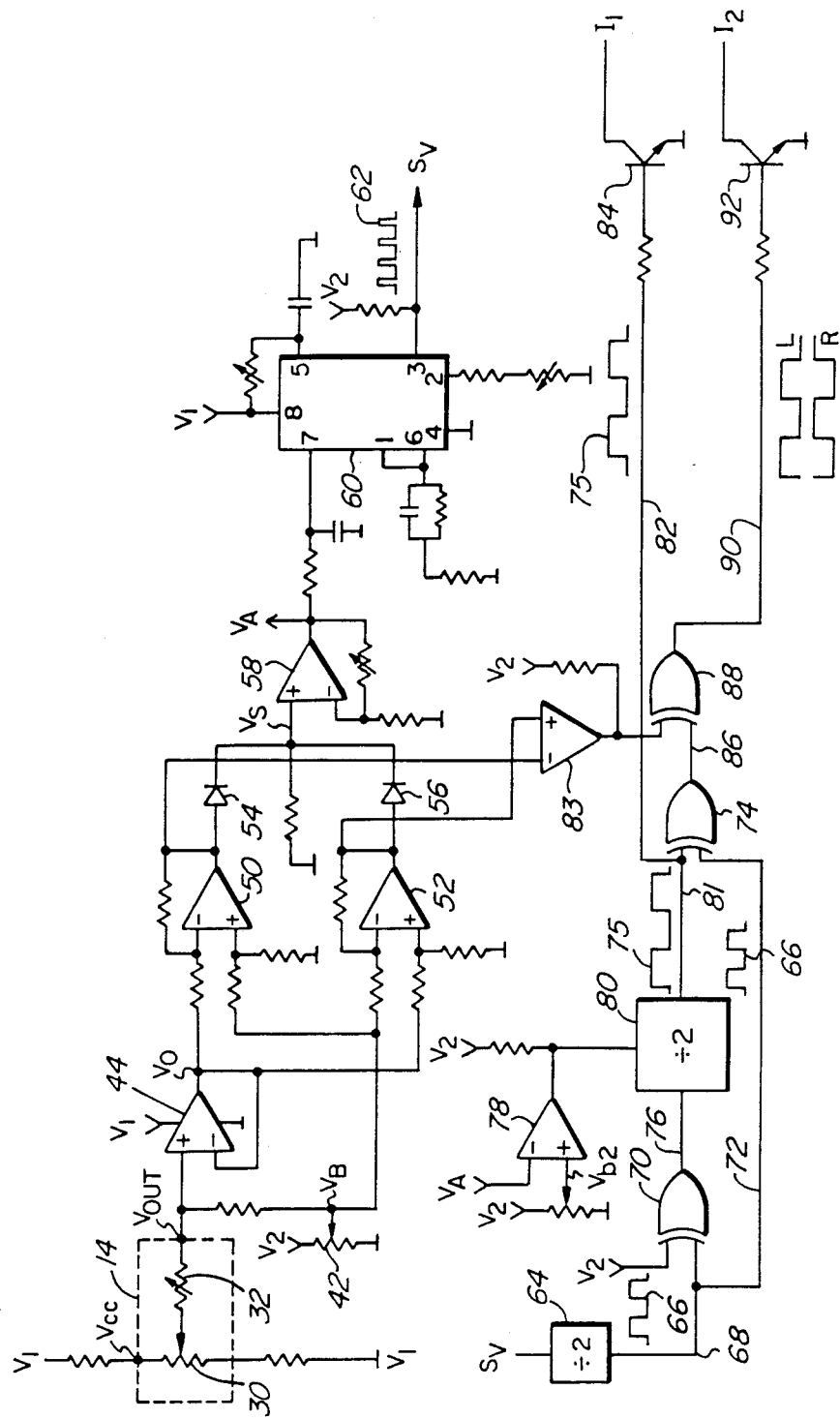
FIG. 6 is a circuit diagram of a circuit that may be used in the present invention including circuitry to convert the signal to operate a computer mouse.

The circuit of FIG. 6 will be provided in effect in duplicate one controlling y direction movement of the element to be moved and the other determining x direction movement. However the circuit will only be described once.

As shown in FIG. 6 input voltage $V_I$ is applied to the system particularly the pad 14 to generate a voltage $V_{cc}$ which will be applied to each of the interdigitized conductor layers 24 and 26 of the pad 14 and an output voltage $V_{out}$ is obtained which as above described varies with distance from the datum zone and the magnitude of the pressure applied at the activated location (pressure point). The force sensitive resistor pad 14 with the applied voltage $V_{cc}$ generates output voltages (for the X and Y controls) continuously over its entire surface, however, the electronics of the system by providing an offset voltage and a threshold voltage forms an apparent dead area or zone 40 as will be described below.

The output voltage $V_{out}$ is buffered from the remainder of the system by a unity amplifier 44 and provides an output voltage $V_0$ which is applied to the negative terminal of a first quad comparator 50 and the positive input of a second quad comparator 52.

A high impedance adjustable source 42 provides a preset biasing voltage $V_B$ which is connected to the positive terminal of comparator 50 and the negative terminal of comparator 52.

It will be apparent that when $V_0$ is greater than $V_B$ that comparator 52 will conduct. On the other hand if $V_0$ is less than $V_B$ comparator 50 will conduct. Thus the biasing voltage $V_B$ determines whether movement along the x axis is to be to the left, for example, if comparator 50 conducts, or to the right if comparator 52 conducts (non-inverting and inverting inputs).

The output voltage generated either by the comparator 50 or the comparator 52 is always positive. This voltage is then conducted through diodes 54 or 56 to provide a signal voltage $V_S$ which is amplified in the amplifier 58 to produce an amplified voltage $V_A$ which is fed directly to a voltage control oscillator (VCO) 60 that generates a square wave having a frequency dependent on the magnitude of the voltage $V_A$. The VCO 60 may be biased in a selected way so that the frequency of the velocity signal $S_V$ may have a selected frequency for a given input voltage $V_A$. The velocity signal $S_V$ will be in the form of a square wave pulse as indicated at 62 having a frequency varying in accordance with the position of the pressure point and the applied force (tongue position and tongue pressure) which generates the voltage $V_S$ and thus the voltage $V_A$. This signal $S_V$ is then preferably divided to form a symmetric cycle pulse, more uniform wave configuration by the binary counter divider 64 which converts the square wave form generally indicated at 62 to the square wave form generally indicated at 66. This converted signal is carried by line 68 to one terminal of the EXCLUSIVE-OR gate 70 and via line 72 to one terminal of the EXCLUSIVE-OR gate 74.

The EXCLUSIVE-OR gate 70 inverts the signal so that the signal leaving the EXCLUSIVE-OR gate 70 in line 76 is essentially the same as the signal in line 68 but inverted. The line 76 connects to a binary counter divider 80 which in turn is connected via line 81 to the other terminal of the EXCLUSIVE-OR gate 74 and via line 82 to the transistor and form the first output $I_1$.

To provide a dead zone in the datum area of the pad 14, the signal voltage $V_A$ is carried to a comparator 78 to which a selected biasing voltage $V_{b2}$ is applied so that the comparator 78 only conducts when $V_A$ is less than $V_{b2}$ which interrupts the output of the binary counter divider 80. If $V_A$ exceeds the biasing voltage $V_{b2}$ comparator 78 switches off $V_2$ which allows the counter divider 80 to output the divided signal. ($V_2$ is a low voltage source generally +5 volts while $V_1$ referred to above will normally be about +15 volts.)

When the divider 80 is operative the frequency of signal 66 (inverted) is reduced by a factor of 2 so that the frequency of signal in line 81 leading to the other side of EXCLUSIVE-OR gate 74 (relative to line 72)

and in line 82 leading to the transistor 84 is as illustrated at 75. The divider 80 is operative only when the voltage $V_A$ is greater than $V_{b2}$ and when it is not active no signal is provided in line 82 thus no signal $I_1$ is generated.

When the signals in line 72 and line 81 are applied to the EXCLUSIVE-OR gate 74 a signal out of phase by 90 degrees compared to the signal in line 82 is generated and passed via line 86 to one terminal of the EXCLUSIVE-OR gate 88.

At the same time, depending on whether the comparator 50 or 52 is transmitting a voltage, a voltage is applied either to the plus or minus inputs of comparator 83 which, depending on whether it is conducting or non-conducting permits the biasing voltage $V_2$ to be applied to the other terminal of the EXCLUSIVE-OR gate 88. If voltage $V_2$ is not applied to the EXCLUSIVE-OR gate 88, the phase signal in line 90 is the same as that in line 86. However if voltage $V_2$ is applied to the EXCLUSIVE-OR gate 88 depending on the status of the comparator 83 the signal in line 90 is shifted 180 degrees (see signals L and R.) Thus, depending on the shift of the signal relative to the signal in line 82, the direction of movement, i.e. to the left, right (or up and down) is determined and this signal in line 90 is fed via transistor 92 to provide output $I_2$.

The inputs $I_1$ and $I_2$ are supplied to an interface card in the computer 29 to provide the required output to control the cursor. The frequencies of the signals $I_1$ and $I_2$ directly relate to the velocity at which the cursor will be moving on the computer display and the phase difference between $I_1$ and $I_2$ will determine the direction of cursor movement, i.e. left and right or up and down.

Figure 7:
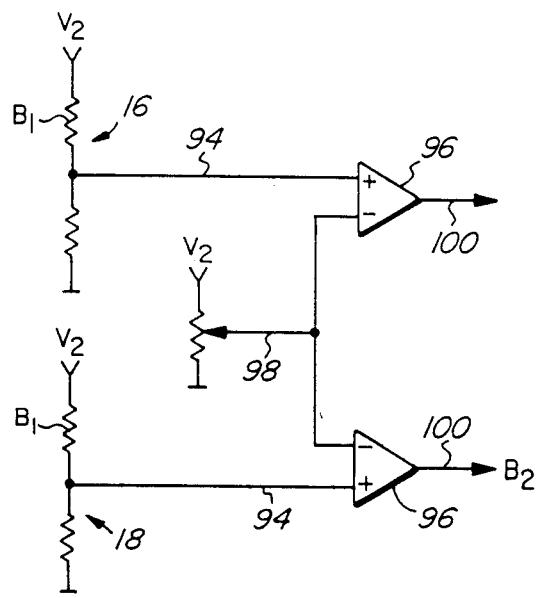
FIG. 7 is a circuit diagram for a pressure sensitive switch that may be incorporated in the present invention.

The button functions, namely the two switches 16 and 18, are preferably realized when incorporating a force sensing resistor B1 (both circuits are essentially the same and thus similar reference numerals will be used for each circuit shown in FIG. 7) and the output from these resistors B1 are directed via lines 94 to comparators 96. A suitable preselected biasing voltage is provided in the line 98 which determines a threshold voltage that the voltage lines 94 must exceed for either of the comparators 96 to generate a signal to actuate the computer 29, i.e. the lines 100 are connected to an interface card in the computer 29.

The above described system has been directed to a system designed for use in place of a Microsoft ™ mouse, but it will be apparent that with suitable modification the control could be used with other mouse systems or to control other vector movements or other devices requiring direction and magnitude inputs.

Having described the invention modifications will be evident to those skilled in the art without departing from the spirit of the invention as defined in the appended claims.

We claim:

1. A XY control system for selecting direction and magnitude of velocity in said selected direction of a controlled means comprising a XY digital pad generating different signals depending on a selected activated location on said pad, electrical circuit means dividing said signals into a datum signal when said activated location on said pad is in a datum zone on said pad, a X signal when said activated location is displaced in a first direction from said datum zone, a Y signal when said activated location is displaced in a second direction perpendicular to said first direction from said datum zone and directional signals for said X and Y signals based on the side of said datum zone in said first and second directions respectively that said activated location is positioned on said pad, said electrical circuit means converting said X and Y signals into velocity signals proportional to the displacement of said activated location relative to said datum zone, and further electrical circuit means controlling said direction and magnitude of said velocity of said controlled means in accordance with said directional and said velocity signals.

2. A system as defined in claim 1 wherein said controlled means comprises a computer cursor and said further circuit means further includes means to convert said directional and velocity signals into signals for obtaining said mutually perpendicular movements of said cursor on a computer monitor.

3. A system as defined in claim 1 wherein said digitizer pad is pressure sensitive and said activated location is activated by pressure applied to said pad at said activated location.

4. A system as defined in claim 3 wherein said digitizer pad is a XYZ digitizer pad and said velocity signals will include a supplementary signal the magnitude of which is dependent on the amount of pressure applied to said activated location.

5. A system as defined in claim 4 wherein said digital pad is mounted on a rigid backing plate sized to be received in the mouth of a user and gripped between the user's teeth with said pad in facing relationship to the user's tongue, said pad having a moisture resistant casing through which tongue pressure may be applied to generate said signals.

6. A control system as defined in claim 5 further comprising at least one pressure sensitive switch mounted on said backing plate adjacent to said pad in a position to be activate by said tongue.

7. A system as defined in claim 3 wherein said controlled means comprises a computer cursor and said further circuit means further includes means to convert said directional and velocity signals into signals for obtaining said mutually perpendicular movements of said cursor on a computer monitor.

8. A system as defined in claim 4 wherein said controlled means comprises a computer cursor and said further circuit means further includes means to convert said directional and velocity signals into signals for obtaining said mutually perpendicular movements of said cursor on a computer monitor.

9. A system as defined in claim 5 wherein said controlled means comprises a computer cursor and said further circuit means further includes means to convert said directional and velocity signals into signals for obtaining said mutually perpendicular movements of said cursor on a computer monitor.

10. A system as defined in claim 6 wherein said controlled means comprises a computer cursor and said further circuit means further includes means to convert said directional and velocity signals into signals for obtaining said mutually perpendicular movements of said cursor on a computer monitor.

* * * * *